US00PP31207P2

(12) United States Plant Patent
Robb

(10) Patent No.: US PP31,207 P2
(45) Date of Patent: Dec. 10, 2019

(54) ***GARDENIA* PLANT NAMED 'PARCUP'**

(50) Latin Name: *Gardenia augusta*
Varietal Denomination: PARCUP

(71) Applicant: John Robb, Kulnura (AU)

(72) Inventor: John Robb, Kulnura (AU)

(73) Assignee: Paradise Seed Company Pty Ltd (AU)

( * ) Notice: Subject to any disclaimer, the term of this patent is extended or adjusted under 35 U.S.C. 154(b) by 0 days.

(21) Appl. No.: 15/999,945

(22) Filed: Aug. 30, 2018

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Gardenia* cultivar named 'PARCUP' is disclosed, characterized by single white flowers having a typical diameter of 5 to 7 cm. Plants are compact, with deep green obovate foliage. The new cultivar is a *Gardenia*, suitable for ornamental garden purposes.

2 Drawing Sheets

Figure 1:
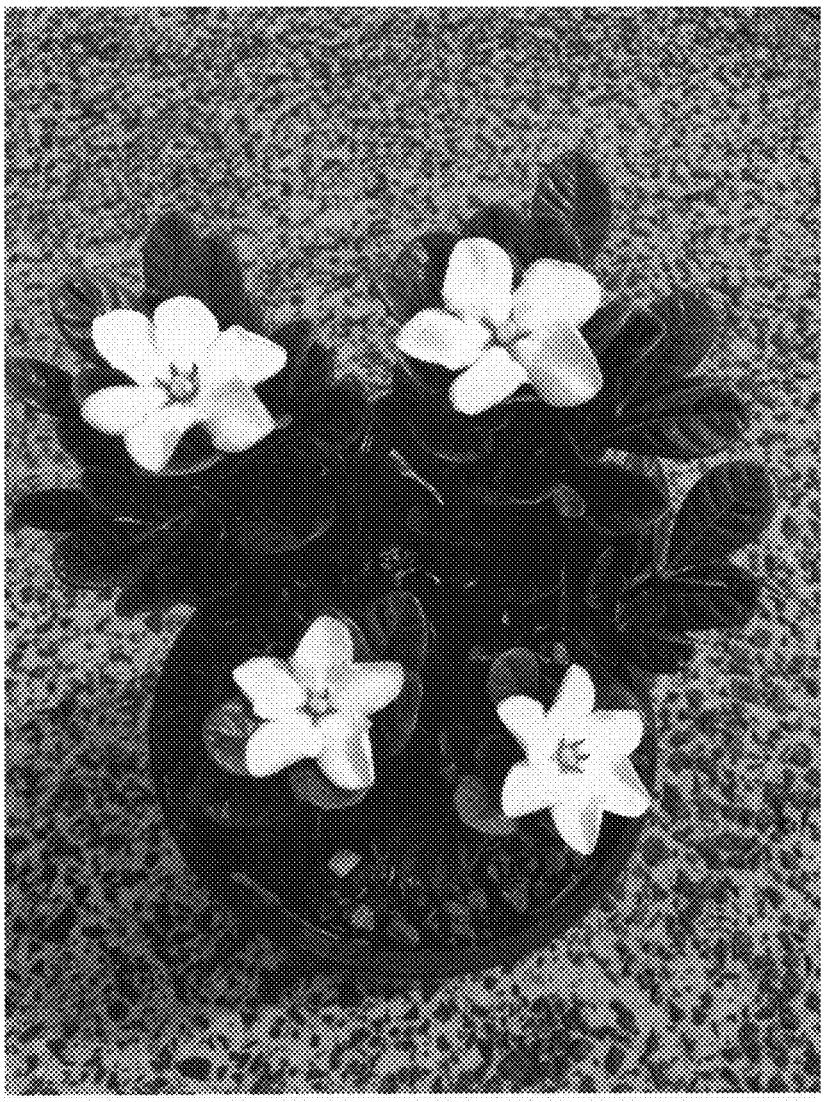

Latin name of the genus and species: *Gardenia augusta*. Variety denomination 'PARCUP'.

BACKGROUND OF THE INVENTION

The new cultivar is a product of a planned breeding program by the inventor. The crossing resulting in the new variety was made in December 2012, at a nursery in Kulnura, Australia. The seed parent is the commercial variety *Gardenia* 'Buttons', U.S. Plant Pat. No. 24,229. The pollen parent is the unpatented commercial variety *Gardenia* 'Grandiflora Star'. The inventor discovered this new variety at the same nursery in March 2016.

After identifying the new variety as a potentially interesting selection, the inventor first organized propagation of 'PARCUP' by semi-hardwood vegetative cuttings during 2016 at the same commercial nursery in Kulnura, Australia. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'PARCUP' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PARCUP' These characteristics in combination distinguish 'PARCUP' as a new and distinct *Gardenia* cultivar:

1. Very compact plant habit.
2. Deep green foliage.
3. Single flowers.

COMPARISON TO PARENT VARIETY

'PARCUP' is similar in most horticultural characteristics to the seed parent variety *Gardenia* 'Buttons', U.S. Plant Pat. No. 24,229. Plants of the new cultivar 'PARCUP' however, differ in the following:

1. The new variety produces a single flower, the seed parent variety produces a semi-double flower.

'PARCUP' is similar in most horticultural characteristics to the pollen parent variety *Gardenia* 'Grandiflora Star', unpatented. Plants of the new cultivar 'PARCUP' however, differ in the following:

1. New cultivar's leaf apex is obtuse; the pollen parent's apex is acute.
2. New variety's leaf undulation is medium to strong; parent's is weak.

COMMERCIAL COMPARISON

'PARCUP' can be compared to the commercial variety *Gardenia hybrida* 'LEETHREE', U.S. Plant Pat. No. 27,599. Plants of the new cultivar 'PARCUP' are similar to plants of 'LEETHREE' in most horticultural characteristics, however, plants of the new cultivar 'PARCUP' differ in the following:

1. Plants of 'LEETHREE' are smaller and more compact than plants of 'PARCUP'.
2. Foliage of the new variety is obovate, with an obtuse apex, foliage of this comparator is elliptic, with an acute apex.
3. Flowers of the new variety are flatter, having a shorter tube length of 1 to 2 cm, compared to the longer 3.5 cm tube length of this comparator.

'PARCUP' is similar in most horticultural characteristics to the commercial variety *Gardenia* 'LEETWO', U.S. Plant Pat. No. 27,601. Plants of the new cultivar 'PARCUP' however, differ in the following:

1. Plants of 'LEETWO' are smaller and more compact than plants of 'PARCUP'.
2. Flowers of the new variety are wider, having a diameter range of 5 to 7 cm, compared to the 4 to 4.5 cm diameter flowers of this comparator.

BRIEF DESCRIPTION OF THE PHOTOGRAPHS

The accompanying photograph in FIG. 1 illustrates in full color a plant of 'PARCUP' grown outdoors in Kulnura, Australia.

Figure 2:
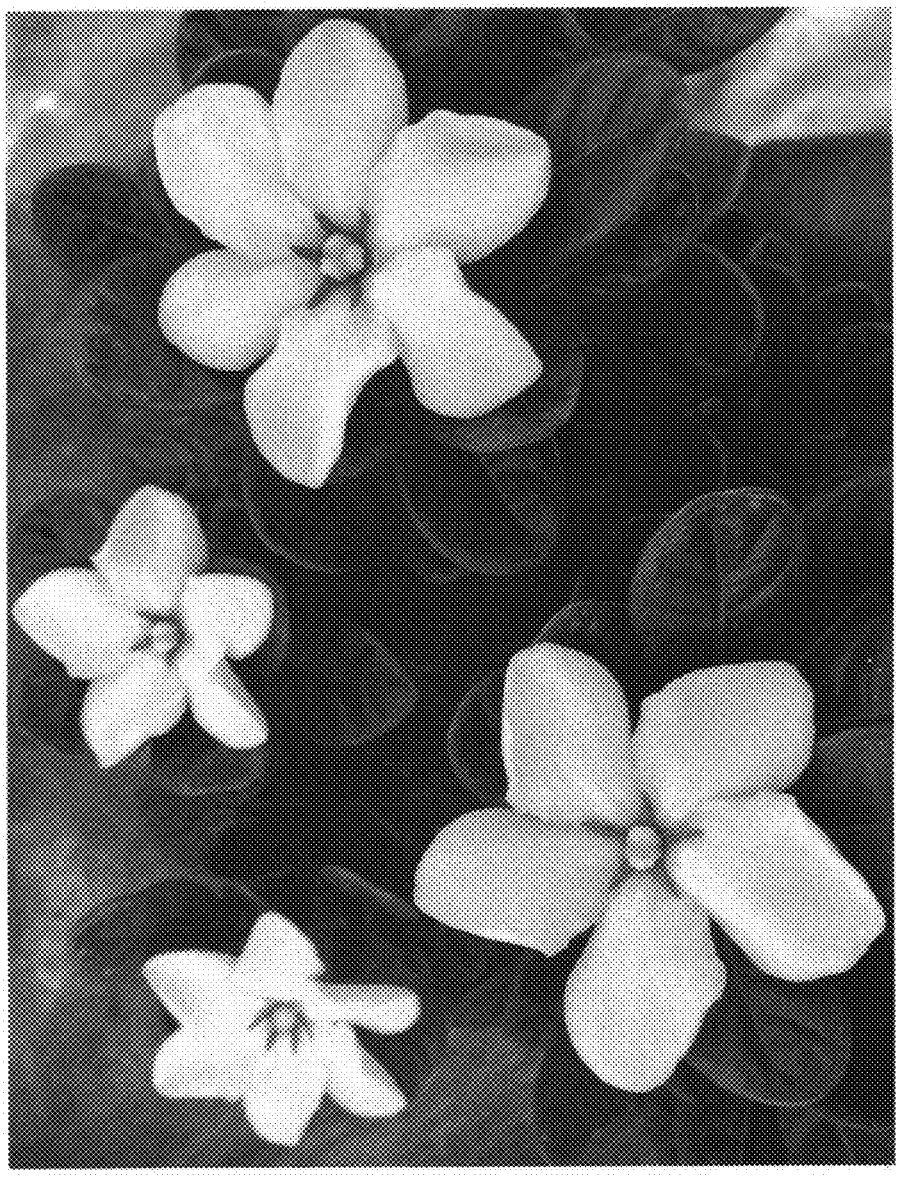

FIG. 2 shows a close up of a typical flower of the new variety. The plant is approximately 2 years old, and is shown in an approximate 200 mm container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'PARCUP' plants grown outdoors in the Summer, in Kulnura, Australia. Plants are approximately 18 months old, in 200 mm pots. Measurements and numerical values represent averages of typical plant types.

Botanical classification: *Gardenia augusta* 'PARCUP'.

PROPAGATION

Typically by semi-hardwood cuttings in spring and summer.
Time to rooting: 30-50 days at approximately 22° C.
Time to produce a rooted plantlet: 100 days.
Root description: White fleshy roots. Not accurately measured with a color chart.

PLANT

Growth habit: Compact.
Height: 75 cm.
Plant spread: 75 cm.
Branching characteristics: Well branched.
Primary branches:
- *Length*.—15-20 cm.
- *Diameter*.—5-6 mm.
- *Strength*.—Strong.
- *Color*.—Dark brown. Near RHS Brown 200A.
- *Texture*.—Rough.

Lateral branches:
- *Color*.—Near RHS Yellow-Green 144A.
- *Length*.—Average range 5-10 cm.
- *Diameter*.—Approximately 3-4 mm.
- *Aspect*.—Erect.
- *Texture*.—Smooth.
- *Strength*.—Strong.
- *Internode*.—Average range 20-30 mm.

Age of plant described: Approximately 18 months.

FOLIAGE

Leaf:
- *Type*.—Simple.
- *Arrangement*.—Whorled.
- *Average length*.—4-6 cm.
- *Average width*.—25-30 mm.
- *Shape of blade*.—Obovate.
- *Apex*.—Rounded.
- *Base*.—Shortly attenuate.
- *Attachment*.—Petiolate.
- *Margin*.—Entire, slightly recurved.
- *Aspect*.—Undulating
- *Leaf internode*.—Average range 20-30 mm.
- *Texture of top surface*.—Rippled.
- *Texture of bottom surface*.—Rippled.
- *Appearance of top surface*.—Glossy.
- *Appearance of bottom surface*.—Matte.
- *Color*.—Young foliage upper side: Near RHS Yellow-Green 146A. Young foliage under side: Near RHS Yellow-Green 144B. Mature foliage upper side: Near RHS Yellow-Green 147A. Mature foliage under side: Near RHS Yellow-Green 144A.
- *Venation*.—Type: Pinnate. Venation color upper side: Near RHS 147A, midrib lighter near RHS 144B. Venation color under side: Near RHS 144A, midrib lighter near RHS 144B.

Petiole:
- *Length*.—1 to 3 mm.
- *Diameter*.—2 mm.
- *Color*.—RHS Yellow-Green 144B.

FLOWER

Bloom period: Spring-Summer.
Peduncle:
- *Length*.—Average 5-10 mm.
- *Diameter*.—Average 3-4 mm.
- *Color*.—Near RHS 144B.
- *Texture*.—Smooth.
- *Aspect*.—Upright.
- *Strength*.—Strong.
- *Aspect*.—Straight. Angle of attachment, approximately 15° angle from stem.
- *Strength*.—Moderately strong and flexible.

Flowers:
Arrangement: Single rotate flowers arise from upper leaf axils.
- *Height*.—Average 10-20 mm.
- *Diameter*.—Average 50-70 mm.
- *Facing direction*.—Upright.
- *Lastingness of individual flowers on plant*.—3 to 4 days.
- *Persistent or self-cleaning*.—Mostly persistent.
- *Fragrance*.—Strong.

Tube:
- *Tube length*.—Approximately 10-20 mm.
- *Tube width a widest point*.—Approximately 4-5 mm.
- *Tube width and narrowest point*.—Approximately 3-4 mm.

Petals:
- *Unfused petal segments*.—Length: Approximately 20-30 mm. Width: Approximately 15-20 mm. Apex: Rounded/obtuse. Base: Fused at base into tube. Color, inner surface: RHS Yellow-Green 150D. Color, outer surface: RHS White 155C. Shape of petal: Elliptic-obovate. Petal margin: Entire, frequently recurved or incurved.
- *Petal arrangement*.—Rotate, slightly overlapping.
- *Petal number*.—5-6.
- *Petal texture upper and lower*.—Smooth.

Color:
- *Upper surface at first opening*.—Near RHS White N155C.
- *Under surface at first opening*.—Near RHS White N155C flushed Yellow-Green 150D.
- *Inner surface at maturity*.—Near RHS White 155C.
- *Outer surface at maturity*.—Near RHS White 155C.
- *Upper surface at fading*.—Near RHS White 155B.
- *Under surface at fading*.—Near RHS White 155B.

Bud:

*Shape*.—Oval.

*Length*.—1-2 cm.

*Diameter*.—1-1.5 cm.

*Color*.—Near RHS Yellow-Green N144B.

Calyx/sepals:

*Quantity per flower*.—6-10.

*Arrangement*.—Whorled.

*Shape*.—Linear-lanceolate.

*Length*.—Average 3-5 mm.

*Width*.—Average 1-2 mm.

*Apex*.—Acuminate.

*Base*.—Broader than apex, fused to receptacle.

*Margin*.—Entire.

*Texture*.—Smooth.

*Color*.—Inner Surface: Near RHS Yellow-Green 144B. Outer Surface: Near RHS Yellow-Green 144B.

REPRODUCTIVE ORGANS

Stamens:

*Number*.—Approximately 5-6.

*Length*.—Approximately 5-10 mm.

*Width*.—Approximately 1-2 mm.

*Anthers*.—Length: Approximately 5-10 mm. Width: Approximately 1-2 mm. Color: Near RHS Yellow-Green 153B. Pollen Quantity and Color: Abundant. Yellow-Green near RHS 153B. Shape: Linear.

Pistil:

*Number*.—1.

*Length*.—Approximately 5-10 mm.

*Style*.—Length: Approximately 10-15 mm. Color: Near RHS 158D. Stigma Shape and Color: Oval-orbicular, near RHS 155A. Ovary Shape, Size, Color: Approximately 5 mm in length, 5 mm in diameter, color near RHS 144C.

OTHER CHARACTERISTICS

No tolerance to drought.

Disease and pest resistance: Neither resistance nor susceptibility to the normal diseases and pests of *Gardenia* observed. Typical diseases of *Gardenia* include *Erysiphe polygoni*,and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: 30° C. to 20° C. during the day. 15° C. to 20° C. during the night.

Fruit/seed production: Not observed to date.

What is claimed is:

1. A new and distinct cultivar of *Gardenia* plant named 'PARCUP' as herein illustrated and described.

* * * * *